United States Patent [19]

Batten

[11] 4,210,401
[45] Jul. 1, 1980

[54] VISIBLE AND INFRARED POLARIZATION RATIO SPECTROREFLECTOMETER

[75] Inventor: Carmen E. Batten, Newport News, Va.

[73] Assignee: The United States of America as represented by the Administrator of the National Aeronautics and Space Administration, Washington, D.C.

[21] Appl. No.: 929,087

[22] Filed: Jul. 28, 1978

[51] Int. Cl.² .................. G01N 21/40; G01J 4/00
[52] U.S. Cl. ................................ 356/369; 356/244
[58] Field of Search ........................ 356/364–370, 356/31, 33–35, 322, 327; 250/225

[56] References Cited

U.S. PATENT DOCUMENTS 4,030,836   6/1977   Smith ........................... 356/369

OTHER PUBLICATIONS

Henty et al. "A Universal Ellipsometer," Surface Science, 56, 1976, pp. 170–181.
Hunderi et al. "A Simple Automatic Ellipsometer for a Wide Energy Range" Surf. Science, 56, 1976, pp. 182–188.

*Primary Examiner*—John K. Corbin
*Assistant Examiner*—Wm. H. Punter
*Attorney, Agent, or Firm*—Wallace J. Nelson; John R. Manning; Howard J. Osborn

[57] ABSTRACT

The instrument disclosed assists in determining the refractive index and absorption index, at different spectral frequencies, of a solid sample by illuminating the sample at various angles in incidence and measuring the corresponding reflected intensities at various spectral frequencies and polarization angles. The ratio of the intensity of the reflected light for parallel polarized light to that for perpendicular polarized light at two different angles of incidence can be used to determine the optical constants of the sample.

The invention involves an apparatus for facilitating the utilization of a wide variety of angles of incidence. The light source and polarizing element are positioned on an outer platform; the sample is positioned on an inner platform. The two platforms rotate about a common axis and cooperate in their rotation such that the sample is rotated one degree for every two degrees of rotation of the light source. This maintains the impingement of the reflected light upon the detector for any angle of incidence without moving or adjusting the detector which allows a continuous change in the angle of incidence.

10 Claims, 7 Drawing Figures

VISIBLE AND INFRARED POLARIZATION RATIO SPECTROREFLECTOMETER

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

This invention relates to an instrument for making reflectance measurements and in particular to a visible and infrared polarization ratio spectroreflectometer for determining the n and k optical constants of a sample material by measuring the intensity of reflected polarized light at various angles of incidence and at various wavelengths.

DESCRIPTION OF THE PRIOR ART

The optical constants of a material can be determined from measurements of reflected polarized light from the material surface. Plane polarized light undergoes a shift in polarization when it is reflected from an object at an oblique angle. The magnitude of this shift depends on the angle of incidence of the light upon the object, and the optical properties of the object; the optical properties of the object depend on the composition of the object and the wavelength of the reflected light.

The ratio of the intensity of the reflected light for parallel polarized light to that for perpendicular polarized light at two different angles of incidence yields two equations and two unknowns from which the n and k optical constant can be calculated for the wavelength of light measured. These equations are:

$$\frac{R_P}{R_S} = \frac{[(a_j - \sin\theta_j \tan\theta_j)^2 + b_j^2]}{[(a_j + \sin\theta_j \tan\theta_j)^2 + b_j^2]}$$

where $$\left(\frac{m}{n_o}\right)^2 - \sin^2\theta_j = (a_j - ib_j)^2$$

and where

Complex index of refraction $m = n - ik$
where
$n$ = refractive index of the sample
$k$ = absorption index of the sample
$n_o$ = refractive index of air
$R_P$ = intensity of parallel polarized light
$R_S$ = intensity of perpendicular polarized light The reflected light also undergoes a change in intensity whose value is related to the polarization shift. Thus, the optical constants can also be found by measuring the intensity of the reflected polarized light of a given wavelength at two known angles of incidence.

The optical constants of soot particles affect the heat transfer in flames and combustion chambers of aircraft engines. This is because the radiant heat flux in combustors and flames is greatly influenced by the radiation emission from the soot particles. The intensity of the emitted radiation is dependent on the soot concentration and on the soot optical constants n and k (the reflective index and the absorption coefficient, respectively). The concentration and the optical constants of the soot generated by a fuel seem to depend on the fuel used. Therefore, the heat transfer properties should vary according to the fuel.

Present optical techniques, such as light scattering, used in heat-flux calculations for measuring soot concentrations require knowledge of the optical constants. These values are not known for soot particles produced by some fuels and those data available disclose the constants for only a limited range of light wavelengths. Since the optical constants of a particle may vary with the wavelength of the light, it is important to know the value over a wide range, especially in the thermal infrared region for heat transfer calculations. Therefore, an instrument capable of easily measuring the optical constants of soot for a wide range of light wavelengths is required before the heat transfer properties of a given fuel can be predicted.

It is also useful to determine the optical constants of soot aerosols in the visible and spectral infrared regions. Soot aerosols in the atmosphere comprise about 50 percent of urban aerosols. These enter the atmosphere by way of smoke stacks, automobile exhaust systems, etc. The soot affects the solar energy transfer through the atmosphere, the visibility through the atmosphere, pollution levels of the atmosphere, etc. The optical constants of the soot are necessary to measure concentration levels which are used for atmosphere modeling, weather forecasting, and visibility predictions.

There are instruments available for making reflectance measurements. However, these instruments have severe limitations in that they do not have provisions for a wide spectral range including both visible and infrared light plan polarized at any desirable angle of polarization, and the angle of incidence is either fixed or variable only over a narrow range, usually 55° to 90°, with no capability for continuously changing the angle of incidence. A wide range of angles of incidence is desirable since different substances reflect an optimum intensity of light at different angles.

OBJECTS OF THE INVENTION

It is therefore an object of the present invention to overcome the limitations imposed by previous designs by providing a visible and infrared polarization ratio spectroreflectometer with the capability of continuously changing the angle of incidence of light upon the sample surface.

Another object of the present invention is to provide such a spectroreflectometer having a wide range of angles of incidence.

A further object of the present invention is to provide such a spectroreflectometer having a wide spectral range of source light including both visible and infrared light.

An additional object of the present invention is to provide such a spectroreflectometer that can be easily automated and/or operated by a computer.

Another object of the present invention is to provide such a spectroreflectometer with provision therein for interchangeable polarizers.

A further object of the present invention is to provide such a spectroreflectometer with provision therein for continuous polarizer rotation.

Another object of the present invention is to provide such a spectroreflectometer having the capability for measuring transmission as well as reflectance.

Another object of the present invention is to provide such a spectroreflectometer with provision therein for detector selection by rotating a mirror in the monochromator thus minimizing detector mounting, warmup, and alignment time.

Another object of the present invention is to provide such a spectroreflectometer with provision therein for automatically placing the sample and a reference surface alternatively in the light path to enable sample/reference signal comparison.

An additional object of the present invention is to provide such a spectroreflectometer with provision therein for accepting samples of various thicknesses while maintaining alignment of the sample surface in the optical path.

A further object of the present invention is to provide such a spectroreflectometer that can also determine the optical properties of liquids by modifying the sample holder to hold a commercially available sample cell which can hold liquid samples.

The foregoing and other objects of the invention and many of the attendant advantages thereof will be readily apparent as the same becomes better understood by reference to the following description when considered in conjunction with the accompanying drawings.

SUMMARY OF THE INVENTION

The present invention measures the intensity of polarized light reflected from a sample surface to determine the refractive index and the absorption coefficient of the sample. The instrument comprises an infrared and a visible light source positioned on a rotating arm platform. A selecting mirror on the platform is adjustable to reflect light from the desired source to a chopper, a reflecting mirror, a focusing mirror, and a rotating polarizing element all located on the rotating arm platform. The polarizing element is interchangeable with other such elements, the particular element employed being dependant on which light source is selected. The focusing mirror focuses the light onto the sample surface or onto a reference surface both of which are positioned on a disc that rotated on a horizontal axis. The disc is located on the rotating sample platform which rotates on the same axis as the rotating arm platform. The disc rotates so as to alternately place the sample surface and the reference surface into the light path. The rotating sample platform cooperates with the rotating arm platform such that the former rotates 1° for every 2° that the latter rotates. The effect of the coordinated rotations of these platforms is to direct the light reflected from the sample surface onto the same spot regardless of the angle of incidence of the light upon the sample surface.

A fixed arm platform supports a focusing mirror to focus the reflected light onto the entrance slit of a monochromator. The monochromator contains a selecting mirror which directs the light onto a infrared detector or a visible light detector depending on the source used. The monochromator steps through a wide frequency spectrum by discriminating against all but one frequency of the light at a time which it directs to the appropriate detector. The frequency of the light sent to the detector is continuously adjusted from 0.3–15μ. The detector is connected to a recording instrument which graphs the intensity of the reflected light of various degrees of polarization versus the wavelength of the reflected light.

DETAILED DESCRIPTION OF THE INVENTION

Figure 1:
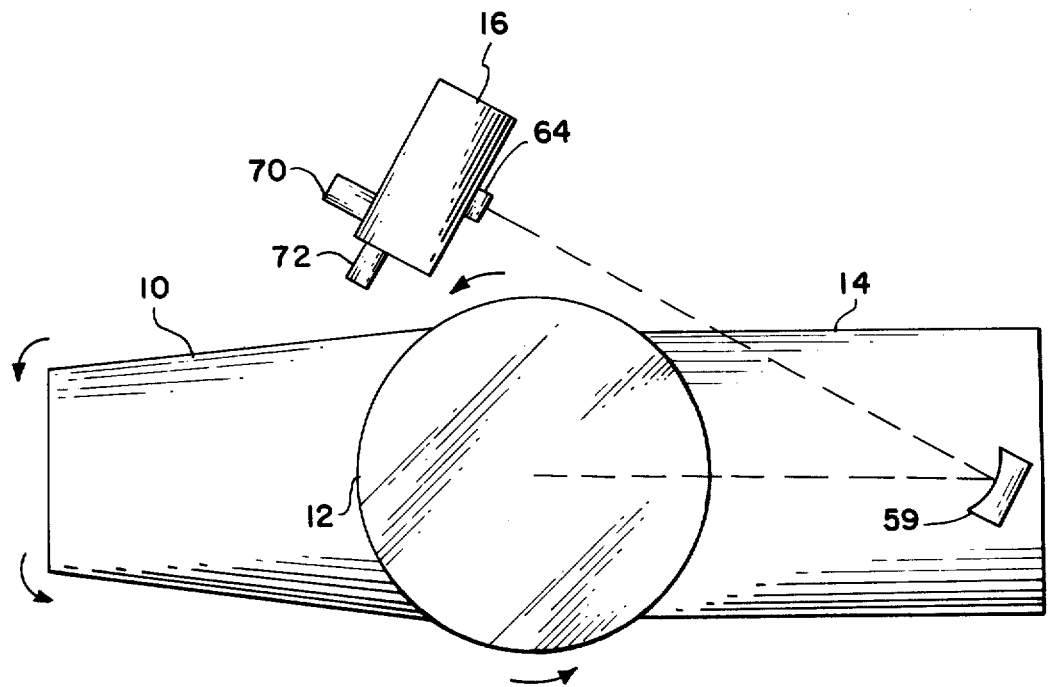
FIG. 1 is a top view of the supporting structures of the present invention.

The invention can be best understood by referring to the accompanying drawings in which like numerals refer to the same components throughout the several views. As shown in FIG. 1, the instrument basically comprises a rotating arm platform 10, a sample rotating platform 12, a fixed arm platform 14, and a monochromator 16.

Figure 2:
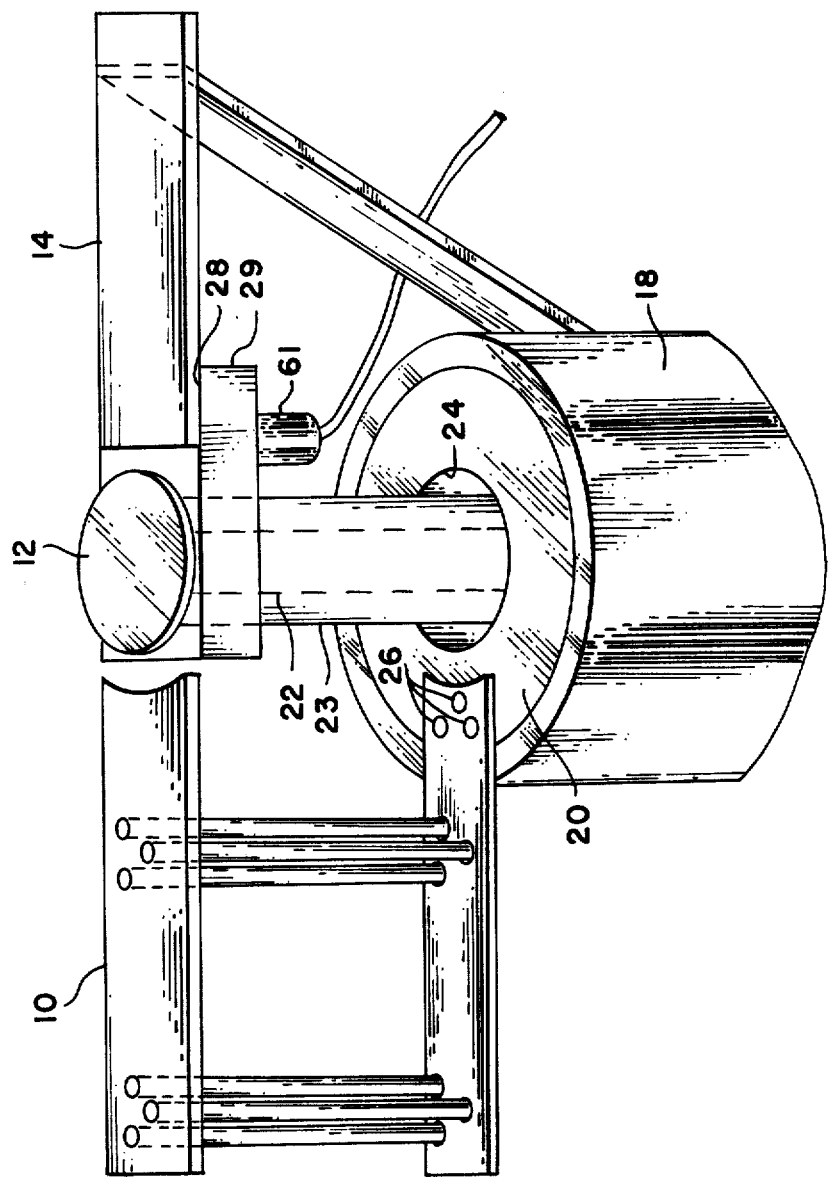
FIG. 2 is a side view of the supporting structures of the present invention.

FIG. 2 displays a base 18 to which platforms 10, 12, and 14 are connected. Hub 20 is connected by base 18 and rotates therein. Rotating arm platform 10 rotates with and is fixedly attached to hub 20 by means of bolts 26. Spindle 22, enclosed by housing tube 23, is supported by base 18, emerges through hole 24 in hub 20, and rotates on the same axis as hub 20. Sample rotating platform 12 is fixedly attached to and rotates with spindle 22. Therefore, rotating arm platform 10 rotates on the same axis as sample rotating platform 12. The rotation of hub 20 is related to the rotation of spindle 22 such that hub 20 rotates 2° for every 1° of rotation of spindle 22. The reduction gears that accomplish this are conventional and located within base 18 and are not shown in the interest of clarity. Encoder 61 reads the angular position of sample rotating platform 12. Fixed arm platform 14 is fixedly attached to base 18. End 28 of fixed arm platform 14 is attached to housing tube 23 via support member 29.

Figure 3:
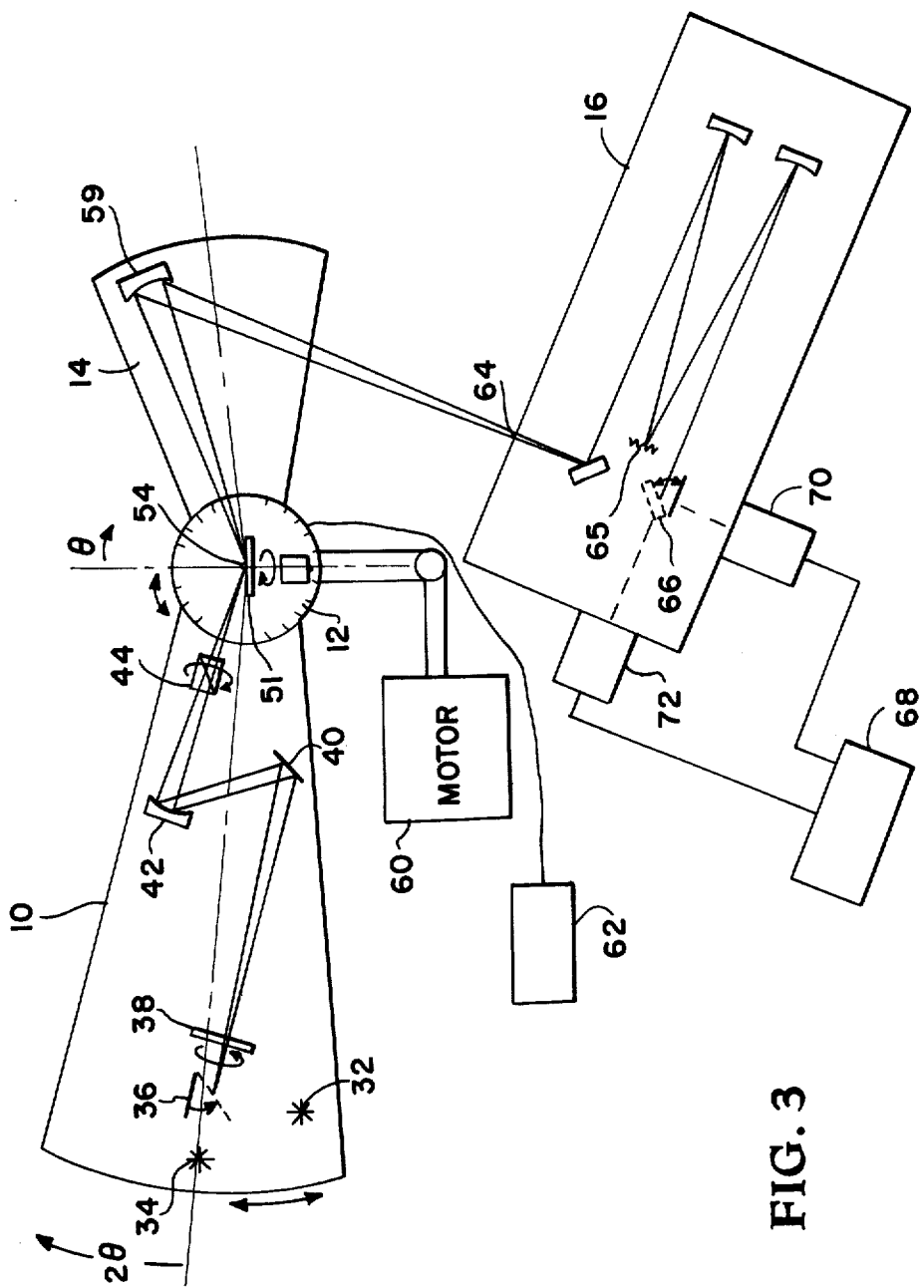
FIG. 3 is a schematic view of the present invention.

FIG. 3 depicts the components mounted on rotating arm platform 10 that act to create the desired signal to be reflected off the sample surface 51. Selecting mirror 36 is a flat reflecting mirror that is manually positioned to select the light from either visible light source 32 or infrared light source 34. The light is chopped by chopper 38 before it reaches reflecting mirror 40 and focusing mirror 42 which focuses the light onto sample 51 to aid in the eventual amplification of the signal. Polarizing element 44 polarizes the light for reasons described above before it strikes sample 51.

Figure 4:
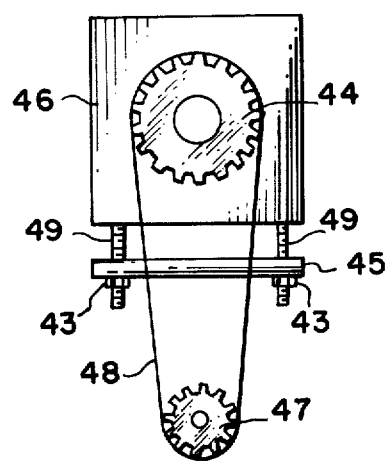
FIG. 4 is a back view of the polarizer and polarizer holder.

FIG. 4 illustrates how polarizing element 44 fits into polarizer holder 46 to allow interchangeable polarizers. The polarizer holder is fastened to rotating arm platform 10 by means of brace 45 which is placed on the underside of rotating arm platform 10 and screws 49 which extend from holder 46 through brace 45 and are fastened by nuts 43. Thus, an infrared polarizer may be easily inserted when infrared source 34 is being used and a visible light polarizer may be inserted when visible light source 32 is being used. Holder 46 permits rotation of the polarizer while synchronous motor 47 drives belt 48 to rotate the polarizer.

Figure 5:
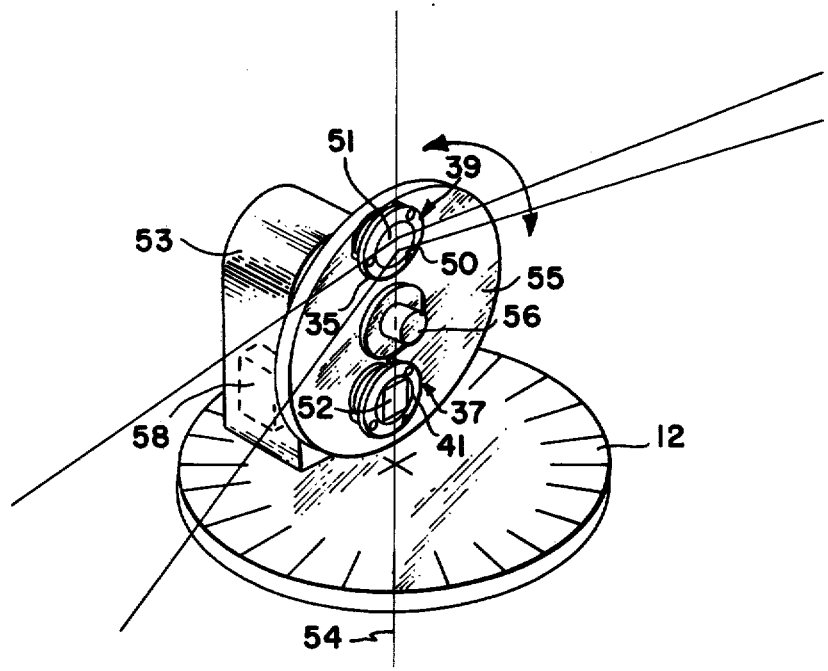
FIG. 5 is a perspective view of the sample rotating platform and sample spinner disc.

The sample rotating platform 12 and the components mounted thereon are best seen in FIG. 5. Sample spinner disc 55 supports sample holder 50 and reference holder 41 by means of mounts 37 and 39. The reference holder supports a mirror 52. Spinner disc 55 is releasably attached to spindle 56 of post 53 which is rigidly attached to sample rotating platform 12 such that the surface of sample 51 positioned in sample holder 50 and the surface of reference mirror 52 positioned in reference holder 41 will coincide with axis 54 of rotating platform 12. The spinner disc 55 rotates on spindle 56 so as to be capable of alternately placing reference surface 52 and sample surface 51 into the light path.

Figure 6:
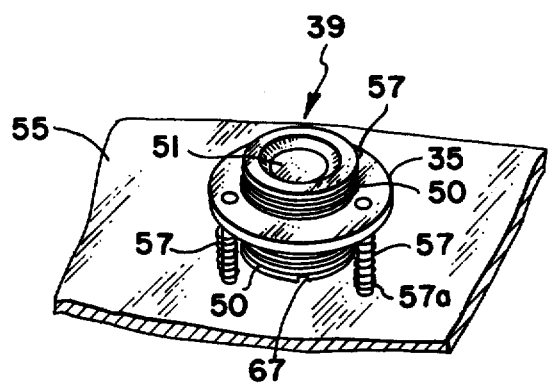
FIG. 6 is a perspective view of the sample holder and mount.

Mounts 37 and 39 are identical so only mount 39 will be described in the interest of brevity. Mount 39 comprises a ring 35 through which a plurality of screws 57 (three shown in the preferred embodiment) extend as seen in FIG. 6. The screws 57 are encircled by springs 57a. The screw-spring arrangement allows adjustments to be made in the positioning of holder 50 to compensate for surface irregularities and ensure a surface reflection that lies along the plane of spinner disc 55.

Ring 35 is threaded along its inside surface to accept holder 50 which is intruded along its outside surface. By rotating holder within mount 39 sample 51 is moved closer to or farther from spinner disc 55. This allows a fine adjustment to ensure that the surface of sample 51 coincides with axis 54 of rotating platform 12. The bottom of holder 50 contains groove 67 or similar structure to facilitate this adjustment.

Spinner disc 55 is interchangeable with other spinner discs (not shown) that are adapted to hold different size sample holders (not shown). The different size sample holders serve to support samples of different sizes (not shown).

The rotation of spinner disc 55 is independent of the rotation of polarizer 44 and rotating platforms 10 and 12 and is controlled by motor 58.

The fixed arm platform 14 and components mounted thereon are best seen in FIG. 1. Focusing mirror 59 receives the light reflected from the sample 51 and focuses it onto the entrance slit of monochromator 16 (FIG. 3). Monochromator 16 contains grating 65 that reflects only the desired frequency of light to selecting mirror 66 which directs the monochromatic light onto infrared detector 70 or visible light detector 72 depending on whether visible light source 32 or infrared light source 34 is being used. Recorder 68 graphically records the intensity of reflected light versus the wavelength of the reflected light.

OPERATION OF THE INVENTION

The operation of the invention is now believed apparent. Referring to FIG. 3, selector mirror 36 is adjusted to select light from either infrared light source 34 or visible light source 32 as shown respectively in the dotted and solid positions. Selector mirror 36 directs the light through variable speed chopper 38, the frequency of chopper 38 is selected according to the spectral range of the light. The light is then reflected by flat mirror 40 which directs the light onto focusing mirror 42. Focusing mirror 42 focuses the light through polarizer 44 onto sample 51 (FIG. 5) or reference mirror 52 depending upon the position of sample spinner disc 55. Polarizer 44 polarizes the light before it reaches the sample surface. Polarizer 44 may be set at a particular angle setting or it may be continuously rotating thereby continuously changing the angle of polarization from 0°–360°.

Figure 7:
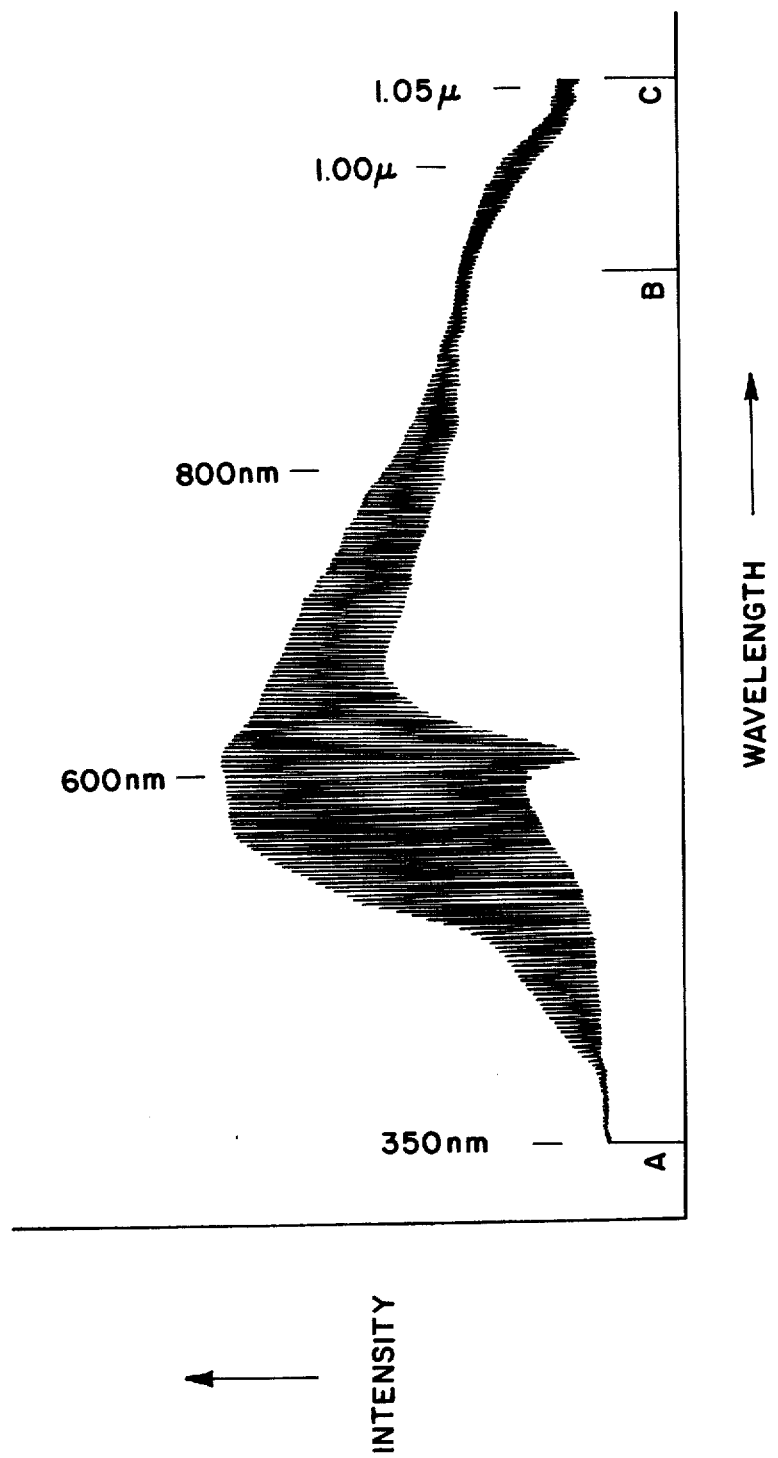
FIG. 7 is a graph of reflected intensity versus wavelength for a sample soot surface.

The polarized light strikes the sample surface 51 at the desired angle of incidence which is selected by rotating the rotating arm platform 10. Since sample rotating platform 12 rotates such that the light will always strike focusing mirror 59 at the same angle regardless of the angle of incidence, the angle of incidence may be continuously changed while the measurements are being made without further realignment of the optical components. In an embodiment of the invention motor 60 operates at two speeds to rotate rotating arm platform 10 and sample rotating platform 12 at either 0.2° or 2° per minute. Obviously motors operating at other speeds could be used. Counter 62 reads the information sent by encoder 61 (FIG. 2) and displays the angle of incidence. The light is reflected from the sample at an angle whose magnitude is equal to that of the angle of incidence but with a change in polarization phase. The polarization phase change is a function of the angle of incidence, and of the optical constants of the sample material. This phase change is accompanied by a proportional change in the intensity of the light. The light is reflected by the sample 51 onto focusing mirror 59 which focuses the light onto the entrance slit of monochromator 64. The monochromator provides spectral range discrimination by means of gratings 65 and sends light of the selected wavelength to selector mirror 66 which reflects the light onto the face of the appropriate detector be it infrared or visible. Recorder 68 is connected to the detectors 70 and 72 and graphs the intensity of light versus the wavelength of the light. FIG. 7 is exemplary of such a graph produced by recorder 68. A kerosene soot particle constituted the sample surface for this test. The angle of incidence was 80° and the polarizer was constantly rotating. The maxima of the graph from points A to B show the intensity of the perpendicular polarized light; the minima show the intensity of the parallel polarized light. From points B to C, the maxima show the parallel polarized light and the minima the perpendicular polarized light. The optical constants can be determined by examination of these graphs as is well known in the art.

It is seen, therefore, that among other things the invention aids in the prediction of heat transfer in flames and combustion chambers of aircraft engines by providing an instrument with which the optical constants of a sample material may be easily determined. The automatic aligning feature of the invention greatly simplifies these measurements and in particular this feature allows the discovery of the best angle of incidence to use for a particular sample to maximize the reflected intensity of the light and thereby improve the accuracy of the measurements.

It is to be understood that the specific description of the invention contained therein is illustrative only and that the actual invention is not so limited. Modification and variations of the invention will be apparent to one skilled in the art. For example, it may be desirable to provide more than two light sources and polarizers, and/or the sample spinner disc could be adapted to support a large number of sample surfaces. Another variation of the invention would be to replace the fixed arm platform with another rotating arm platform. The sample rotating platform would be made stationary. A detector would be placed on one rotating platform, the light source on the other rotating platform. The two platforms would cooperate with each other such that the one platform would rotate −1° for every 1° the other platform rotates. Likewise, the sample holder could be modified to hold a commercially available sample cell which can hold liquid samples. Thus, the invention could determine the optical properties of liquids and water solutions.

These and other changes in the illustrated features of the invention which are readily apparent to those skilled in the art in the light of the above teachings do not depart from the spirit and scope of the appended claims and are intended to be included therein.

What is new and desired to be secured by Letters Patent of the United States is:

1. An instrument for measuring the intensity of polarized light reflected from a surface, the combination comprising:
   (a) a sample surface;
   (b) a reference surface;
   (c) multiple light sources;
   (d) light selection and chopping means for selecting the light from one of said multiple light sources, chopping the light signal at a predetermined frequency, and focusing the light onto said sample surface;
   (e) continuously rotating light polarizing means positioned between said sample surface and said light selection and chopping means and wherein said continuously rotating light polarizing means continuously changes the plane of polarization of the light from 0° to 360°;
   (f) detection means for selectively sensing and analyzing light reflected from said sample surface and said reference surface;
   (g) sample spinner means connected to said light selection and chopping means and positioned between said light selection and chopping means and said detection means for supporting said sample surface and said reference surface; and
   (h) aligning means for automatically aligning said light selection and chopping means, said sample spinner means, and said detection means while the angle of incidence is changed continuously or otherwise, so that the light from said light selection and chopping means upon striking said sample surface will reflect from said sample surface and impinge on said detection means.

2. An instrument as in claim 1 wherein said detection means comprises:
   a monochromator;
   an infrared detector;
   a visible light detector; and
   a selecting mirror within said monochromator for selectively directing the light onto either said infrared detector or onto said visible light detector.

3. An instrument as in claim 1 wherein said light selection and chopping means comprises:
   (a) a rotatable selecting mirror for selecting the light from one of said multiple light sources;
   (b) a reflecting mirror that receives the light reflected from said source selecting mirror;
   (c) a chopper disposed between said source selecting mirror and said reflecting mirror for chopping the light signal at a predetermined frequency; and
   (d) a focusing mirror for receiving the light reflected from said reflecting mirror and focusing the light into said sample surface.

4. An instrument as in claim 1 wherein said multiple light sources comprise:
   a first light source;
   a second light source;
   said first light source being a visible light lamp; and
   said second light source being an infrared light lamp.

5. An instrument as in claim 1 wherein said continuously rotating light polarizing means comprises:
   (a) a rotatable polarizer holder positioned between said light selection and chopping means and said sample surface;
   (b) a polarizer motor drive for rotating said polarizer holder to change the plane of polarization of the light from 0° to 360°; and
   (c) a polarizing element releasably attached to said polarizer holder to provide polarized incident light directly on said sample surface;
   wherein said polarizing element is selected from a plurality of interchangeable polarizing elements including a visible light polarizer and an infrared light polarizer.

6. An instrument as in claim 1 wherein said aligning means comprises:
   (a) a rotating arm platform;
   (b) a rotating sample platform; said rotating arm platform rotating about the said axis as said rotating sample platform; the rotation of said arm platform being coupled with the rotation of said sample platform such that the angular rotation of said arm platform is twice that of said sample platform; said sample spinner means being positioned on said rotating sample platform;
   (c) a fixed arm platform;
   (d) a focusing mirror; said fixed arm platform supporting said focusing mirror which receives the light reflected from said sample surface and focuses the light onto said detection means; and
   (e) drive means for rotating said sample platform and said arm platform.

7. An instrument as in claim 6 wherein said drive means comprises:
   a motor for rotating said sample platform and said arm platform automatically; and
   a crank for selectively rotating said sample platform and said arm platform manually.

8. An instrument for measuring the intensity of polarized light reflected from a surface, the combination comprising:
   (a) a sample surface;
   (b) a reference surface;
   (c) source means for generating a light signal that impinges on said sample surface and said reference surface;
   (d) detection means for selectively sensing and analyzing light reflected from said sample surface and said reference surface;
   (e) a rotating arm platform;
   (f) a rotating sample platform;
      said rotating arm platform rotating about the same axis as said rotating sample platform; the rotation of said arm platform being coupled with the rotation of said sample platform such that the angular rotation of said arm platform is twice that of said sample platform;
   (g) a fixed arm platform;
   (h) a focusing mirror;
   said fixed arm platform supporting said focusing mirror which receives the light reflected from said sample surface and focuses the light onto said detection means;

(i) drive means for rotating said sample platform and said arm platform;

(j) a sample holder positioned on said rotating sample platform;

(k) a reference holder for holding said reference surface positioned on said rotating sample platform;

(l) a post rigidly attached to and perpendicular to said sample platform;

(m) a rotatable sample spinner disc, said spinner disc being adapted to accept said reference holder and said sample holder, said spinner disc being releasably attachable to said post and rotatable thereon about an axis perpendicular to the axis of rotation of said sample platform so as to place said sample surface and said reference surface alternately in the path of the light directed by said source means;

(n) a pair of mountings attached to said sample spinner disc to accept said sample holder and said reference holder, said sample holder and said reference holder being cylindrical with the bottom surfaces thereof provided with a diametric groove, the outside surfaces thereof being threaded and the top portion of said sample holder being recessed to receive said sample surface, said mountings being annular rings threaded on the inside surface thereof to receive and support, respectively, said sample holder and said reference holder, said sample holder and said reference holder being rotatable within said mountings so that said sample surface and said reference surface coincide with the axis of rotation of said sample platform, said mountings being adjustable by screws extending through springs positioned between said mounting and the front surface of said sample spinner disc, said screws being positioned near the perimeter of said mountings at equal intervals to enable compensatory adjustments for surface irregularities of said sample surface and said reference surface; and (o) a motor to rotate said sample spinner disc upon said post.

9. An instrument as in claim 8 wherein said sample holder is selected from a plurality of sample holders of varying sizes to accept samples of varying sizes.

10. An instrument as in claim 9 wherein said sample spinner disc is selected from a plurality of diverse size sample spinner discs each adapted to accept a sample holder of a particular size.

* * * * *